United States Patent [19]
Arkangel

[11] 4,001,896
[45] Jan. 11, 1977

[54] PROSTHETIC JOINT FOR TOTAL KNEE REPLACEMENT

[75] Inventor: Robert Arkangel, Warsaw, Ind.

[73] Assignee: Zimmer, U.S.A. Inc., Warsaw, Ind.

[22] Filed: Jan. 26, 1976

[21] Appl. No.: 652,587

Related U.S. Application Data

[63] Substitute for Ser. No. 584,796, June 9, 1975, abandoned.

[52] U.S. Cl. .................................. 3/1.91; 3/1.911; 128/92 C
[51] Int. Cl.[2] .......................................... A61F 1/24
[58] Field of Search .................... 3/1.9–1.913, 3/1, 22; 128/92 C, 92 CA

[56] References Cited
UNITED STATES PATENTS

| | | | |
|---|---|---|---|
| 3,765,033 | 10/1973 | Goldberg et al. | 3/1.911 |
| 3,818,512 | 6/1974 | Shersher | 3/1.912 |
| 3,824,630 | 7/1974 | Johnston | 3/1.911 |

*Primary Examiner*—Ronald L. Frinks
*Attorney, Agent, or Firm*—Richard H. Brink; David J. Mugford

[57] ABSTRACT

The embodiment of the invention disclosed herein is directed to a joint prosthesis for total knee replacement. The joint prosthesis includes a first prosthetic member including a stem member adapted for insertion into a first skeleton element. A second prosthetic member includes a stem for insertion into a second skeleton element which is disposed adjacent to first skeleton element. The joint prosthesis is provided with a removable plateau member which forms a slide or rubbing surface for the prosthetic members. The removable plateau can be replaced when worn. Retaining screws are provided on opposite sides of the first prosthetic member to retain the ball within the socket therein.

3 Claims, 3 Drawing Figures

PROSTHETIC JOINT FOR TOTAL KNEE REPLACEMENT

RELATED APPLICATIONS

This application is a substitute for abandoned application Ser. No. 584,796 filed Jun. 9, 1975.

BACKGROUND OF THE INVENTION

This invention relates to a prosthetic joint, and more particularly to a prosthetic joint for total knee replacement. The prosthetic joint is adapted to be implanted in the body of a subject human or animal.

Heretofore, prosthetic joints have been used to replace defective natural joints in humans and animals when such joints have become diseased or injured through accident. However, prior art prosthetic members have not been wholly satisfactory for knee implantation because they do not provide for the complexity involved when flexing the tibia relative to the femur. Furthermore, the prior art prosthetic joints do not provide for replacement of wear surfaces without completely removing the implanted unit. Some prior art prosthetic joints tend to become inoperative because of wear. This may reduce their ability to perform the complicated movements inherent in natural knee joints. While suitable prosthetic members have been devised utilizing simple ball joint construction, it has been found that a surface-to-surface contact of the external parts of the joint provide better movement. This surface-to-surface external contact of the spaced-apart prosthetic members cause wear of the surfaces and in time replacement is required.

Accordingly, it is an object of this invention to provide a new and improved joint prosthesis for total knee replacement which enables replacement of worn parts without necessitating the complete removal of the implanted units.

Briefly, the femoral member of the joint prosthesis includes two locking pins designed to prevent the ball and socket components from subluxating after insertion. The tibial member is provided with a boss to receive a recess in a plateau which forms a bearing surface between the femoral and tibial members. The plateau structure allows a surgeon to replace it in the event of significant wearing of the bearing material. Also the ball and socket unit can be replaced by the construction of the present invention.

Instead of being pressed over a narrow pin, which makes replacement very difficult, the plateau slides over a metal boss formed on the upper surface of the tibial member and is held in place by a ball stud anchor screw. The ball stud is inserted into a blind hole and held in place by the ball stud anchor screw which extends transversely therethrough. Therefore, threading of the ball stud into the tibial member is unnecessary and thereby facilitates removal of the components.

In order to avoid the possibility of the anchor screw moving or backing out of the boss member, cruciate slots have been cut into the posterior aspect of the anchor screw to provide diametrically opposed locking tab members at the end thereof. The locking tab members are flared out to conform to the shape of a chamfer on the posterior aspect of the metal boss of the tibial component. If replacement of the ball and/or plateau is necessary, the anchor screw can be easily removed with a socket head hexagon wrench. During removal of the ball and/or plateau, the femoral and tibial components inserted into the corresponding bone members remain intact.

Many of the obvious features and advantages of this invention will be more fully realized and understood from the following detailed description when taken in conjunction with the accompanying drawings wherein like reference numerals throughout the various views of the drawings are intended to designate similar elements and components.

DETAILED DESCRIPTION OF THE ILLUSTRATED EMBODIMENT

Figure 1:
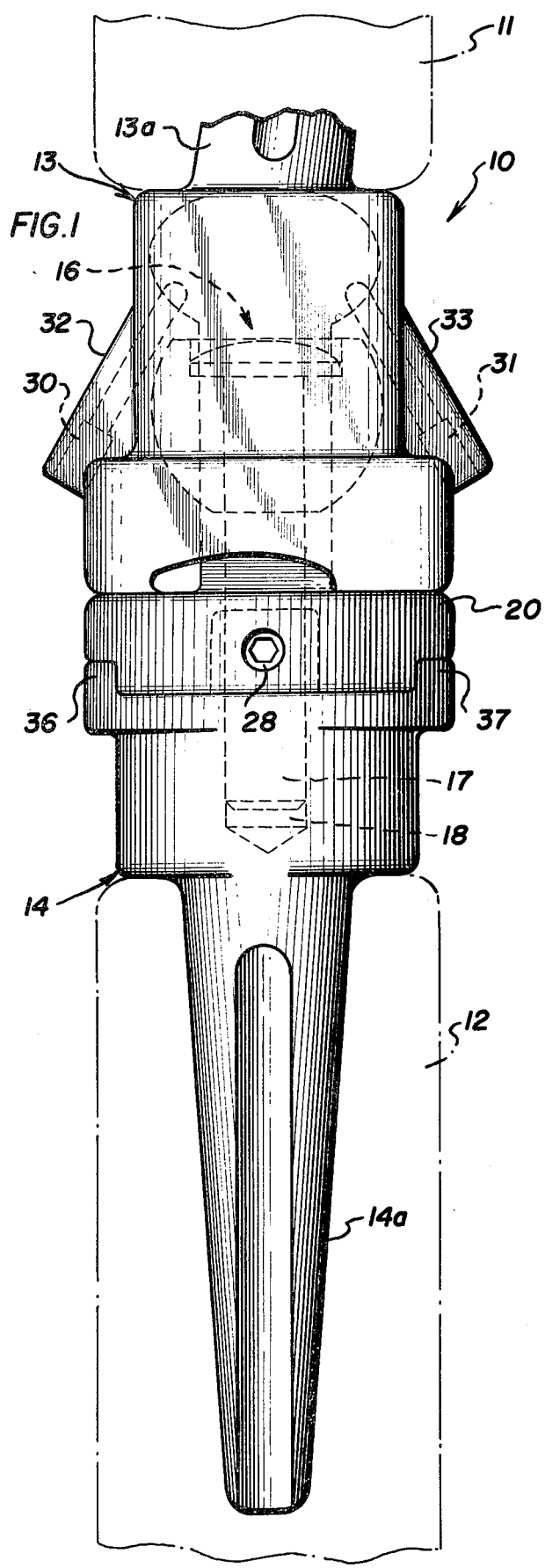
FIG. 1 is an assembled view of a joint prosthesis constructed in accordance with the principles of this invention.
Figure 2:
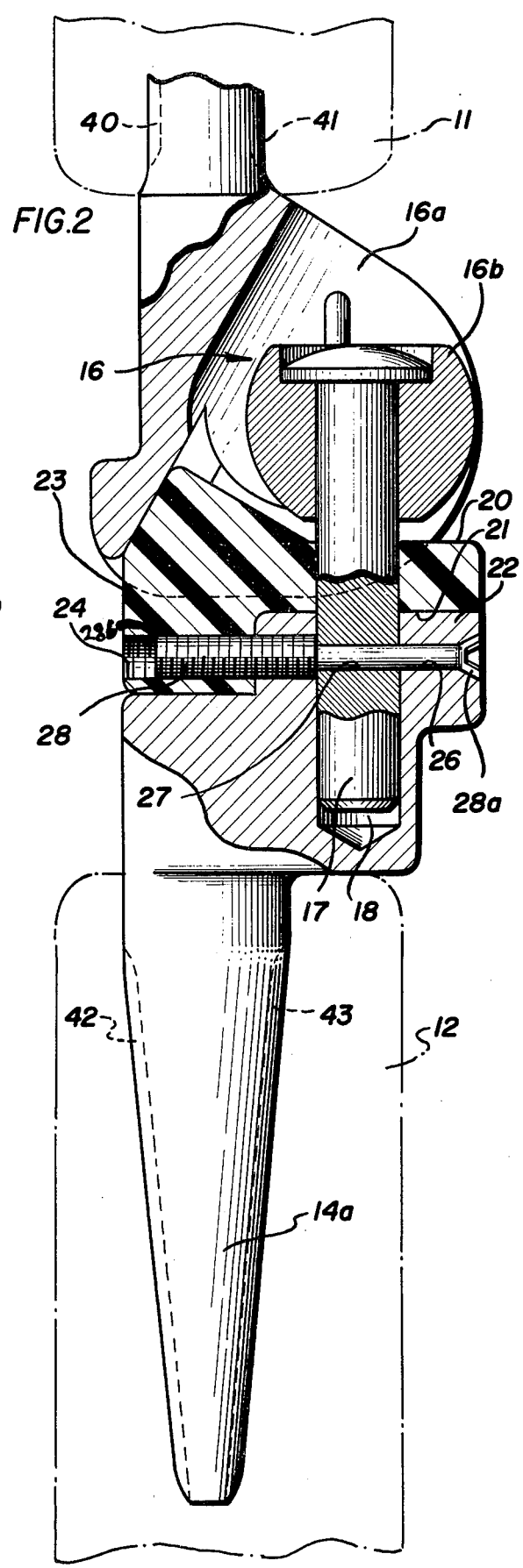
FIG. 2 is a side sectional view of the joint prosthesis of FIG. 1.
Figure 3:
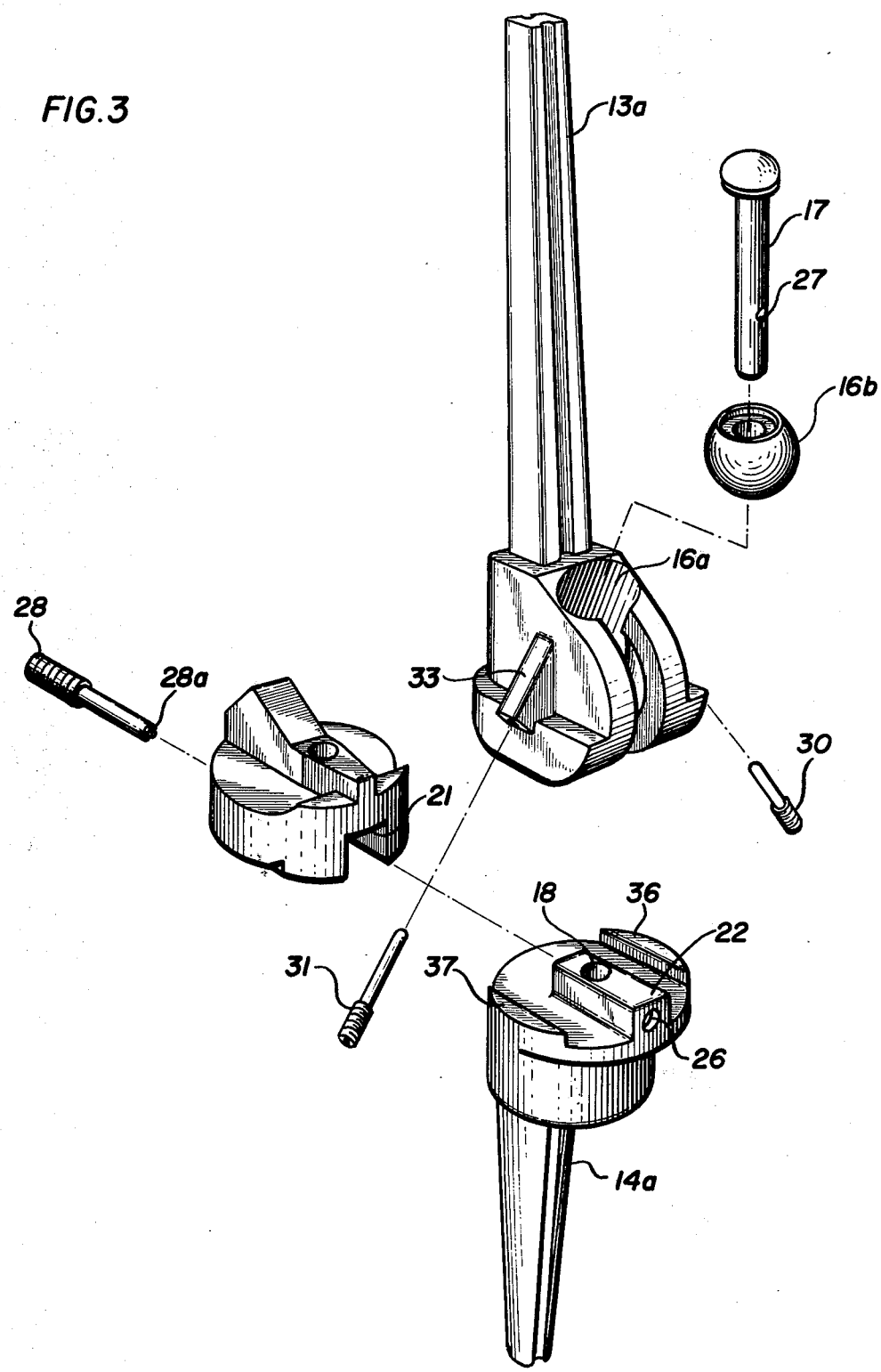
FIG. 3 is an exploded view illustrating the removal of components in accordance with the principles of this invention.

Referring now to the drawings there is seen a joint prosthesis which is constructed in accordance with the principles of this invention and designated generally by reference number 10. The joint prosthesis 10 is shown in relation to its connection to the end portions 11 and 12 of the associated distal femur and proximal tibia, respectively. The prosthesis joint number 10 is formed of a first prosthetic member 13 inserted into the femur and a second prosthetic member 14 inserted into the tibia. The distal end of the femur, and proximal end of the tibia are prepared by cutting and/or reaming the end portions so that the prosthetic members 13 and 14 can have their associated stem elements 13a and 14a inserted in such a manner as to function similar to the pivotal sliding action of the medial condyle and lateral condyle of the actual bone elements being replaced. The prosthetic member 13 is joined with the prosthesis member 14 by means of a ball and socket configuration indicated generally by reference numeral 16 and an anchor pin 17. The anchor pin 17 is nonthreaded and is slidably fitted into an aperture 18 formed in the tibial member.

Most advantageously, a plateau member 20 is removably secured to the tibia member 14 so that it can be replaced if necessary without removing the femur stem 13a or tibia stem 14a from the bone structures. The plateau member 20 has a recess 21 formed therein to be positioned over a boss member 22 formed on the tibia member. The plateau has a front wall portion 23 which has an aperture 24 extending therethrough and which is placed in position with an aperture 26 formed in the boss 22. The anchor pin 17 has an aperture 27 which is placed in alignment with apertures 24 and 26 and an anchor screw 28 passes through the aligned apertures. The anchor screw 28 preferably has a socket head hexagon wrench fitting 28b formed at one end thereof to facilitate removal of the anchor screw when the plateau is to be changed. Also when the anchor screw is removed the anchor pin 17 can be removed to facilitate replacement of the ball member 16b positioned within the socket 16a of the ball and socket unit 16.

To maintain the ball 16b within the socket 16a in its proper position locking pins 30 and 31 are provided through angularly disposed boss members 32 and 33, respectively. The locking pins may be threaded and also provided with the socket head recessed screws to facilitate removal if necessary. The tibia member has upwardly directed flanges 36 and 37 formed on the side portions thereof so that flat side margins of the plateau are held firmly in place.

To insure that the stem member 13a is held securely within femur 11 longitudinal slots 40 and 41 are provided thereby providing biting edge sections to prevent rotational movement relative to the femur. Similarly, slots 42 and 43 are provided in the stem of 14a to grip the tibia and prevent rotational movement therebetween.

The joint prosthesis disclosed herein therefore provides a simple and efficient means for replacing parts which may wear as a result of normal use without requiring complete removal of the structure from the femur and tibia. By loosening and removing the threaded pin 28 the plateau 20 can be removed. Similarly the ball 16b can be replaced is desired.

To insure that the threaded pin 28 does not inadvertently loosen from its position it is provided with a cruciate slot which is flared at 28a to conform to a chamfer within the aperture 26 of the boss 22.

What has been described is a simple and efficient joint prosthesis structure for implantation in the human skeleton, and which joint prosthesis is readily disassembled after implantation to facilitate replacement of worn parts, if necessary. While a single specific embodiment of the present invention has been disclosed herein it will be understood that the variations and modifications may be effected without departing from the spirit and scope of the novel concepts of this invention.

The invention is claimed as follows:

1. A joint prosthesis comprising a first prosthetic member for fixation to a first skeleton element and including a convexly shaped articulation surface for location at the distal end of said first skeleton element, a second prosthetic member for fixation to a second skeleton element adjacent said first skeleton element, and having a boss extending upward therefrom said boss having an aperture extending therethrough link means interconnecting first and second prosthetic members for pivotal movement relative to one another, a removable plateau secured to said second prosthetic member having a recess to receive said boss and prevent rotational movement of said plateau relative to said second prosthetic member and including a front wall portion immediately in front of said boss to define an end wall surface of said recess, aligned apertures extending through said front wall portion and said boss and said member providing an engagement surface for said first prosthetic member, said link means pivotally connecting said first and second prosthetic members to provide a sliding engagement between said convexly shaped articulation surface and said engagement surface of said plateau, and removable fastener means including a threaded shaft having one end thereof split, a chamfer formed at one end of said boss to receive the split end of the threaded shaft, whereby the split end can be spread to retain the threaded shaft in position, said shaft extending through said aligned apertures of said plateau and said boss to retain said plateau to said second prosthetic member, whereby said plateau can be selectively removed and replaced when worn.

2. The joint prosthesis according to claim 1 wherein said link means includes a ball engaging a socket formed in the said first prosthetic member and a ball pin extending therefrom into said second prosthetic member and lock screws positioned on opposite sides of said second prosthetic member to retain said ball in said ball socket by restricting the access aperture of said socket.

3. The joint prosthesis according to claim 1 wherein said first and second prosthetic members include elongated stem members to be inserted into skeleton elements, said elongated members having slots formed therein.

* * * * *